(12) United States Patent
Schmitt et al.

(10) Patent No.: US 6,420,317 B1
(45) Date of Patent: Jul. 16, 2002

(54) BENZOYLPYRAZOLES AND THEIR USE AS HERBICIDES

(75) Inventors: Monika Schmitt, Frankfurt; Andreas van Almsick, Oberursel; Rainer Preuss, Idstein; Lothar Willms, Hofheim; Thomas Auler, Bad Soden; Hermann Bieringer, Eppstein; Felix Thürwächter, Bad Homburg, all of (DE)

(73) Assignee: Aventis CropScience GmbH, Frankfurt (DE)

( * ) Notice: Subject to any disclaimer, the term of this patent is extended or adjusted under 35 U.S.C. 154(b) by 0 days.

(21) Appl. No.: 09/821,261

(22) Filed: Mar. 29, 2001

(30) Foreign Application Priority Data

Mar. 31, 2000 (DE) .......................... 100 16 116

(51) Int. Cl.$^7$ .......................... A01N 43/56; C07D 23/20
(52) U.S. Cl. .................... 504/282; 548/369.4
(58) Field of Search .................. 548/369.4; 504/282

(56) References Cited

U.S. PATENT DOCUMENTS 4,063,925 A    12/1977   Konotsune et al.
4,643,757 A    2/1987    Baba et al.

FOREIGN PATENT DOCUMENTS

| DE | 25 13 750 | 10/1975 |
| EP | 0 203 428 | 12/1986 |
| JP | 08-28442  | 9/1978  |
| JP | 55-33454  | 3/1980  |

*Primary Examiner*—Robert W. Ramsuer
(74) *Attorney, Agent, or Firm*—Frommer Lawrence & Haug LLP

(57) ABSTRACT

Benzoylpyrazoles of the formula (I) and their use as herbicides are described.

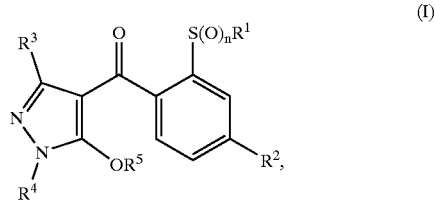

In the formula (I), $R^1$, $R^2$, $R^3$, $R^4$ and $R^5$ are various radicals and n is from 0 to 2.

10 Claims, No Drawings

BENZOYLPYRAZOLES AND THEIR USE AS HERBICIDES

Description

Benzoylpyrazoles and their use as herbicides

The invention relates to the technical field of the herbicides, in particular of the herbicides for the selective control of broad-leaved weeds and weed grasses in crops of useful plants.

It is already known from various publications that certain benzoylpyrazoles have herbicidal properties. Thus, the German laid-open publication D-A 25 13 750 describes 1-alkyl-4-benzoyl-5-hydroxypyrazoles and 1-alkyl-4-benzoyl-5-thiopyrazoles which are preferably substituted on the phenyl ring by one or two radicals. In addition to hydrogen, radicals mentioned as being preferred for the 2-position are bromine, chlorine, iodine, methyl and nitro, for the 3-position methoxy, for the 4-position chlorine, methoxy, methylsulfonyl and nitro and for the 5-position methyl. The hydroxy or thio group of the compounds described therein is optionally substituted by various radicals, such as acyl radicals. J5 5033-45 mentions further 5-hydroxypyrazoles and 5-thiopyrazoles in which the hydroxy or thio group is in principle substituted by various radicals. U.S. Pat. No. 4,643,757 discloses, as herbicides, 1-methyl4-benzoylpyrazoles which preferably carry halogen, nitro or sulfonylmethyl in the 2-position of the phenyl ring, hydrogen, halogen or methyl in the 3-position and halogen or sulfonylmethyl in the 4-position. EP-A 0 203 428 discloses, as herbicides, 1-alkyl-4-benzoylpyrazoles which preferably carry halogen or methyl in the 2-position of the phenyl ring, hydrogen or methyl in the 3-position and halogen or sulfonylmethyl in the 4-position.

However, the compounds known from these publications frequently have an insufficient herbicidal activity and/or insufficient crop plant compatibility. Accordingly, it is an object of the present invention to provide herbicidally active compounds having improved herbicidal properties and improved crop plant compatibility than the compounds known from the prior art.

It has now been found that certain 4-benzoylpyrazoles which are substituted at specific positions by selected radicals are particularly suitable for use as herbicides. Accordingly, the present invention provides compounds of the formula (I) or salts thereof

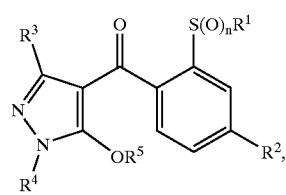

(I)

in which
R$^1$ is methyl or ethyl;
R$^2$ is trifluoromethyl;
R$^3$ is hydrogen, methyl or ethyl;
R$^4$ is methyl, ethyl or n-propyl;
R$^5$ is hydrogen, (C$_1$–C$_6$)-alkylcarbonylmethyl, (C$_1$–C$_4$)-alkylsulfonyl, phenylsulfonyl, benzyl, benzoylmethyl, (C$_1$–C$_3$)-alkylsulfonyl which is mono- or polysubstituted by halogen, phenylsulfonyl which is monosubstituted by methyl or halogen, benzyl which is substituted by halogen, nitro or methoxy or benzoylmethyl which is mono- or polysubstituted by halogen, nitro, methyl or methoxy and
n is 0, 1, or 2.

If R$^5$ is hydrogen the compounds of the formula (I) according to the invention can, depending on external conditions such as solvent and pH, be present in different tautomeric structures:

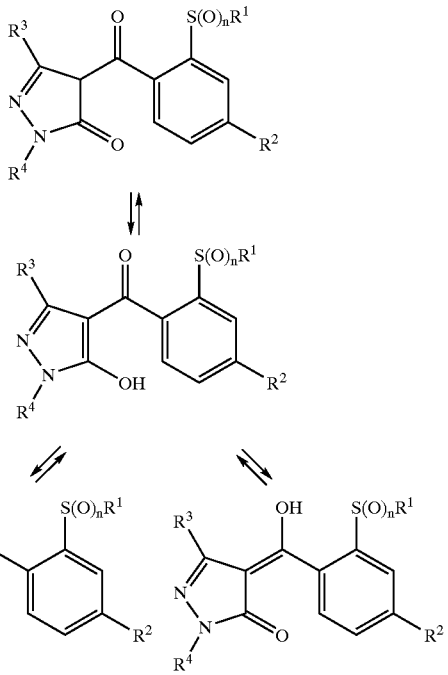

Depending on the type of substituents, the compounds of the formula (I) may contain an acidic proton which can be removed by reaction with a base. Suitable bases are, for example, hydrides, hydroxides and carbonates of lithium, sodium, potassium, magnesium and calcium, and also ammonia and organic amines, such as triethylamine and pyridine. Such salts are likewise provided by the invention.

In formula (I) and all other formulae hereinbelow, alkyl radicals having more than two carbon atoms can be straight-chain or branched. Alkyl radicals are, for example, methyl, ethyl, n- or isopropyl, n-, iso, t- or 2-butyl, pentyls, hexyls, such as n-hexyl, isohexyl and 1,3-dimethylbutyl. Halogen is fluorine, chlorine, bromine or iodine. Tosyl is 4-methylphenylsulfonyl.

If a group is polysubstituted by radicals, this is to be understood as meaning that this group is substituted by one or more identical or different of the radicals mentioned.

Depending on the type and the attachment of the substituents, the compounds of the formula (I) can be present as stereoisomers. If, for example, one or more asymmetrically substituted carbon atoms are present, enantiomers and diastereomers may occur. Stereoisomers can be obtained from the mixtures obtained in the preparation by customary separation methods, for example by chromatographic separation processes. It is also possible to prepare stereoisomers by using stereoselective reactions, employing optically active starting materials and/or auxiliaries. The invention also relates to all stereoisomers and mixtures thereof which are embraced by the formula (I) but not defined specifically.

Of particular interest are compounds of the formula (I), in which n is 2.

Preference is given to compounds of the formula (I), in which
$R^1$ is methyl and
$R^3$ is hydrogen or methyl.

Preference is also given to compounds of the formula (I), in which
$R^4$ is methyl or ethyl.

Particular preference is given to compounds of the formula (I), in which
$R^5$ is methylsulfonyl, ethylsulfonyl, n-propylsulfonyl, phenylsulfonyl, 4-methylphenylsulfonyl, benzyl, benzoylmethyl, nitrobenzoylmethyl or 4-fluorobenzoylmethyl.

Particular preference is likewise given to compounds of the formula (I), in which
$R^5$ is hydrogen.

Very particular preference is given to compounds of the formula (I), in which
$R^3$ is methyl.

In all of the formulae mentioned hereinbelow, the substituents and symbols have the same meaning as described under formula (I), unless defined otherwise. Compounds according to the invention in which $R^5$ is hydrogen can be prepared, for example, by the process shown in Scheme 1 and known from DE-A 25 13 750 by base-catalyzed reaction of a benzoyl halide with a pyrazolone, or according to the process shown in Scheme 2 and known, for example, from EP-A 0 186 117 by base-catalyzed reaction of a benzoyl halide with a pyrazolone and subsequent rearrangement.

Scheme 1

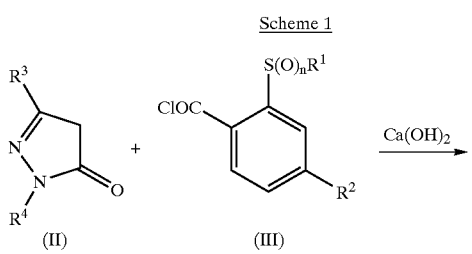

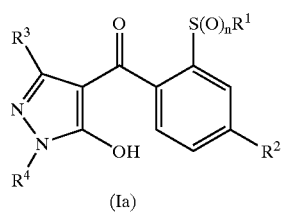

(Ia)

Scheme 2

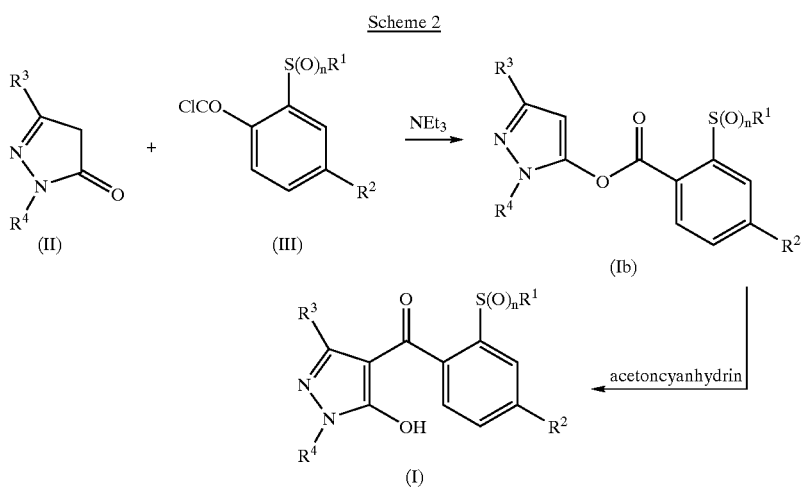

Compounds according to the invention in which $R^5$ is different from hydrogen are, according to Scheme 3, expediently prepared from the compounds obtainable according to Scheme 1 or 2 by base-catalyzed reaction with a suitable acylating agent $R^5$—X in which X is a leaving group such as halogen. Such methods are known, for example, from DE-A 25 13 750.

Scheme 3

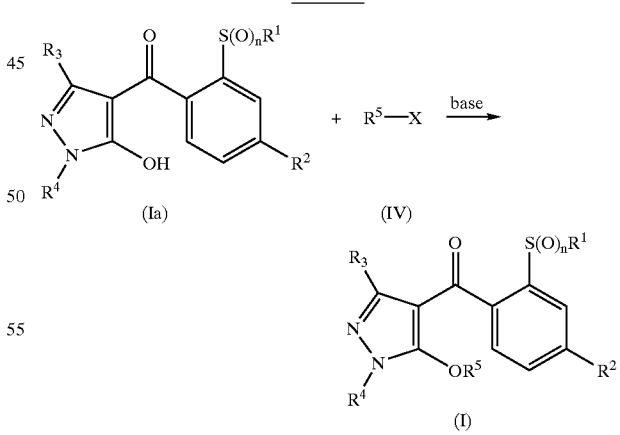

The starting materials used in the schemes above are either commercially available or can be prepared by methods known per se. Thus, the pyrazolones of the formula (II) can be prepared, for example, by the methods described in EP-A 0 240 001 and J. Prakt. Chem. 315, 382, (1973), and the benzoyl chlorides of the formula (III) can be prepared by the process as described in EP-A 0 527 036.

The compounds of the formula (I) according to the invention have an outstanding herbicidal activity against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is generally immaterial whether the substances are applied pre-sowing, pre-emergence or post-emergence. Specifically, examples may be mentioned of some representatives of the monocotyledonous and dicotyledonous weed flora which can be controlled by the compounds according to the invention, without these being a restriction to certain species. Examples of weed species on which the active compounds act efficiently are, from amongst the monocotyledons, Avena, Lolium, Alopecurus, Phalaris, Echinochloa, Digitaria, Setaria and also Cyperus species from the annual sector and from amongst the perennial species Agropyron, Cynodon, Imperata and Sorghum, and also perennial Cyperus species.

In the case of the dicotyledonous weed species, the spectrum of action extends to species such as, for example, Galium, Viola, Veronica, Lamium, Stellaria, Amaranthus, Sinapis, lpomoea, Sida, Matricaria and Abutilon from amongst the annuals, and Convolvulus, Cirsium, Rumex and Artemisia in the case of the perennial weeds. The active compounds according to the invention also effect outstanding control of harmful plants which occur under the specific conditions of rice growing such as, for example, Echinochloa, Sagittaria, Alisma, Eleocharis, Scirpus and Cyperus. If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely. If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely. In particular, the compounds according to the invention exhibit excellent activity against Apera spica venti, Chenopodium album, Lamium purpureum, Polygonum convulvulus, Stellaria media, Veronica hederifolia, Veronica persica, Viola tricolor and against Amaranthus, Galium and Kochia species.

Although the compounds according to the invention have an excellent herbicidal activity against monocotyledonous and dicotyledonous weeds, crop plants of economically important crops such as, for example, wheat, barley, rye, rice, corn, sugarbeet, cotton and soya, are not damaged at all, or only to a negligible extent. In particular, they have excellent compatibility in cereals, such as wheat, barley and corn, in particular wheat. For these reasons, the present compounds are highly suitable for selectively controlling undesired plant growth in plantings for agricultural use or in plantings of ornamentals.

Owing to their herbicidal properties, these active compounds can also be employed for controlling harmful plants in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested produce are known.

The use of the compounds of the formula (I) according to the invention or their salts in economically important transgenic crops of useful and ornamental plants, for example of cereal, such as wheat, barley, rye, oats, millet, rice, maniok and corn, or else in crops of sugarbeet, cotton, soya, rapeseed, potato, tomato, pea and other vegetable species is preferred. The compounds of the formula (I) can preferably be used as herbicides in crops of useful plants which are resistant or which have been made resistant by genetic engineering toward the phytotoxic effects of the herbicides.

Conventional ways for preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases of genetically engineered changes in crop plants in order to modify the starch synthesized in the plants (for example WO 92/11376, WO 92/14827, WO 91/19806), transgenic crop plants which are resistant to certain herbicides of the glufosinate- (cf., for example, EP-A 0 242 236, EP-A 0 242 246) or glyphosate-type (WO 92/00377), or of the sulfonylurea-type (EP-A 0 257 993, U.S. Pat. No. 5013659), transgenic crop plants, for example cotton, having the ability to produce Bacillus thuringiensis toxins (Bt toxins) which impart resistance to certain pests to the plants (EP-A 0 142 924, EP-A 0 193 259), transgenic crop plants having a modified fatty acid composition (WO 91/13972).

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone" [Genes and Clones], VCH Weinheim, 2nd edition 1996, or Christou, "Trends in Plant Science" 1 (1996) 423–431). In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the abovementioned gene product.

To this end it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219–3227; Wolter et al., Proc. Natl. Acad. Sci. USA 85 (1988), 846–850; Sonnewald et al., Plant J. 1(1991), 95–106).

The transgenic plant cells can be regenerated to whole plants using known techniques. The transgenic plants can in principle be plants of any desired plant species, i.e. both monocotyledonous and dicotyledonous plants. In this manner, it is possible to obtain transgenic plants which have modified properties by overexpression, suppression or inhibition of homologous (=natural) genes or gene sequences or by expression of heterologous (=foreign) genes or gene sequences.

When using the active compounds according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crops are resistant, and an effect on the growth and the yield of the transgenic crop plants. The invention therefore also provides for the use of the compounds according to the invention as herbicides for controlling harmful plants in transgenic crop plants.

In addition, the substances according to the invention have outstanding growth regulating properties in crop plants. They engage in the plant metabolism in a regulating manner and can this be employed for the targeted control of plant constituents and for facilitating harvesting, for example by provoking desiccation and stunted growth. Furthermore, they are also suitable for generally regulating and inhibiting undesirable vegetative growth, without destroying the plants in the process. Inhibition of vegetative growth plays an important role in many monocotyledon and dicotyledon crops because lodging can be reduced hereby, or prevented completely.

The compounds according to the invention can be applied in the customary formulations in the form of wettable powders, emulsifiable concentrates, sprayable solutions, dusts or granules. The invention therefore also provides herbicidal compositions comprising compounds of the formula (I). The compounds of the formula (I) can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, dusts (DP), capsule suspensions (CS), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes. These individual formulation types are known in principle and are described, for example, in Winnacker-Kuchler, "Chemische Technologie" [Chemical Technology], Volume 7, C. Hauser Verlag Munich, 4th. Edition 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963;

McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuugart 1976; Winnacker-Küchler, "Chemische Technologie" [Chemical Technology], Volume 7, C. Hauser Verlag Munich, 4th Edition 1986.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ethersulfates, alkanesulfonates, alkylbenzenesulfonates, sodium ligninsulfonate, sodium 2,2'-dinaphthylmethane-6,6'-disulfonate, sodium dibutylnaphthalenesulfonate or else sodium oleoylmethyltaurinate. To prepare the wettable powders, the herbicidally active compounds are finely ground, for example in customary apparatus such as hammer mills, fan mills and air-jet mills, and are mixed simultaneously or subsequently with the formulation auxiliaries.

Emulsifiable concentrates are prepared by dissolving the active compound in an organic solvent, for example butanol, cyclohexanone, dimethylformamide, xylene or else relatively high-boiling aromatic compounds or hydrocarbons or mixtures of the solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth. Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers. Water-dispersible granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see for example processes in "Spray-Drying Handbook" 3rd ed. 1979, G. Goodwin Ltd., London; J.E. Browning, "Agglomeration", Chemical and Engineering 1967, pages 147 ff.; "Perry's Chemical Engineer's Handbook", 5th Ed., McGraw-Hill, New York 1973, pp. 8–57. For further details on the formulation of crop protection products, see for example G. C. Klingman, "Weed Control as a Science", John Wiley and Sons Inc., New York, 1961, pages 81–96 and J. D. Freyer, S. A. Evans, "Weed Control Handbook", 5th Ed., Blackwell Scientific Publications, Oxford, 1968, pages 101–103.

The agrochemical formulations generally contain from 0.1 to 99% by weight, in particular from 0.1 to 95% by weight, of active compound of the formula (I). In wettable powders the concentration of active compound is, for example, from about 10 to 90% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, said formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

Suitable active compounds which can be combined with the active compounds according to the invention in mixed formulations or in a tank mix are, for example, known active compounds as described in for example Weed Research 26, 441–445 (1986), or "The Pesticide Manual", 11th edition, The British Crop Protection Council and the Royal Soc. of Chemistry, 1997 and in the literature cited therein. For example the following active compounds may be mentioned as herbicides which can be combined with the compounds of the formula (I) (note: the compounds are either named by the "common name" in accordance with the International Organization for Standardization (ISO) or by the chemical names, if appropriate together with a customary code number): acetochlor; acifluorfen; aclonifen; AKH 7088, i.e. [[[1-[5-[2-chloro-4-(trifluoromethyl)phenoxy]-2nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazine; azimsulfurone (DPX-A8947); aziprotryn; barban; BAS 516 H, i.e. 5-fluoro-2-phenyl4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDAA, i.e. 2-chloro-N,N-di-2-propenylacetamide; CDEC, i.e. 2-chloroallyl diethyldithiocarbamate; chlomethoxyfen; chloramben; chlorazifop-butyl, chlormesulon (ICI-A0051) chlorbromuron; chlorbufam; chlorfenac; chlorflurecolmethyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (for example butyl ester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl) 4,5-dihydro-5-oxo-1H-tetrazol-1-yl]-phenyl]ethanesulfonamide; ethoxyfen and its esters (for example ethyl ester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flumetsulam; flumeturon; flumiclorac and its esters (for example pentyl ester, S-23031); flumioxazin (S482); flumipropyn; flupoxam (KNW-739); fluorodifen; fluoroglycofen-ethyl; flupropacil (UBIC4243); fluridone; flurochloridone; fluroxypyr; flurtamone; fomesafen; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone; imazapyr; imazamethabenz-methyl; imazaquin and salts such as the ammonium salt; ioxynil; imazethamethapyr; imazethapyr; imazosulfuron; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; metham; methabenzthiazuron; methazole; methoxyphenone; methyldymron; metobenzuron; metobromuron; metolachlor; metosulam (XRD 511); metoxuron; metribuzin; metsulfuron-methyl; MH; molinate; monalide; monolinuron; monuron; monocarbamide dihydrogensulfate; MT 128, i.e. 6-chloro-N-(3-chloro-2-propenyl)-5-methyl-N-phenyl-3-pyridazin-amine; MT 5950, i.e. N-[3-chloro-4-(1-methylethyl)-phenyl]-2-methyl-pentanamide; naproanilide;

napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulfentrazon (FMC-97285, F-6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazol-1-carboxamide; thenylchlor (NSK-850); thiazaflu- ron; thiazopyr (Mon-13200); thidiazimin (SN-24085); thiobencarb; thifensulfuron-methyl; tiocarbazil; tralkoxydim; tri-allate; triasulfuron; triazofenamide; tribenuron-methyl; triclopyr; tridiphane; trietazine; trifluralin; triflusulfuron and its esters (for example methyl ester, DPX-66037); trimeturon; tsitodef; vemolate; WL 110547, i.e. 5-phenoxy-1-[3-(trifluoromethyl)phenyl]-1H-tetrazole; UBH-509; D489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulations which are present in commercially available form are, if appropriate, diluted in the customary manner, for example using water in the case of wettable powders, emulsifiable concentrates, dispersions and water-dispersible granules. Products in the form of dusts, granules for soil application or broadcasting and sprayable solutions are usually not further diluted with other inert substances prior to use. The application rate of the compounds of the formula (I) required varies with the external conditions, such as temperature, humidity, the nature of the herbicide used and the like. It can vary within wide limits, for example between 0.001 and 1.0 kg/ha or more of active substance, but it is preferably between 0.005 and 750 g/ha, in particular between 0.005 and 250 g/ha.

The examples below illustrate the invention.

A. CHEMICAL EXAMPLES

The preparation of the starting materials 2-methylsulfenyl-4-trifluoromethylbenzoic acid, 2-methylsulfinyl-4-trifluoromethylbenzoic acid and 2-methylsulfonyl 4-trifluoromethylbenzoic acid was carried out according to EP-A 0 527 036, the 5-hydroxypyrazoles were prepared according to EP-A 0 240 001 or are commercially available.

1. Preparation of 4-(4-Trifluoromethyl-2-methylsulfonylbenzoyl)-5-hydroxy-1-ethyl-3-methylpyrazole Step 1: 1-Ethyl-3-methyl-5-pyrazolyl4-trifluoromethyl-2-methylsulfonylbenzoate 2.1 g (7.8 mmol) of 2-methylsulfonyl-4-trifluoromethylbenzoic acid were dissolved in 90 ml of $CH_2Cl_2$. 2 drops of DMF and 2.98 g (2.4 mmol) of $(COCl)_2$ were added, and the mixture was boiled under reflux for 4 h. The mixture was then concentrated and the residue was taken up in 300 ml of $CH_2Cl_2$ and, at 0° C., admixed with 1.46 g (9 mmol) of 1-ethyl-3-methyl-5-hydroxypyrazole and 4.45 ml of $NEt_3$. The mixture was stirred at room temperature for 4 h and then concentrated, and the residue was purified by chromatography (silica gel, ethyl acetate:hexane=3:2). This gave 1-ethyl-3-methyl-5-pyrazolyl-4-trifluoromethyl-2-methylsulfonylbenzoate as a solid.

Yield: 2.7 g (95% of theory) $R_f$ (ethyl ester): 0.75; $^1$H-NMR: δ [CDCl$_3$] 1.42 (t, 3H), 2.25 (s, 3H), 3.25 (s, 3H), 4.05 (q, 2H), 6.08 (s, 1H), 7.45 (d, 1H), 7.65 (s, 1H), 8.24 (d, 1H).

Step 2: 4-(4-Trifluoromethyl-2-methylsulfonylbenzoyl)-5-hydroxy-1-ethyl-3-methylpyrazole 1.27 g (3.4 mmol) of 1-ethyl-3-methyl-5-pyrazolyl-4-trifluoromethyl-2-methylsulfonylbenzoate, 2 drops of acetone cyanohydrin and 0.8 ml (5.8 mmol) of $NEt_3$ were dissolved in 80 ml of $CH_3CN$, and the mixture was stirred at room temperature overnight. The mixture was then concentrated to dryness and the residue was admixed with water and the mixture was acidified using 2 N HCl. The precipitated product was filtered off with suction and recrystallized from ethanol. This gave 4-(4-trifluoromethyl-2-methylsulfonylbenzoyl)-5-hydroxy-1-ethyl-3-methylpyrazole as a yellowish oil.

Yield: 1.22 g (96% of theory); $^1$H-NMR: δ [CDCl$_3$] 1.45 (t,3H), 2.25 (s, 3H), 2.95 (s, 3H), 4.00 (q, 2H), 7.65 (1H), 7.85 (d,$_1$H), 8.58 (s, 1H).

2. Preparation of 4-(4-Trifluoromethyl-2-methylsulfonylbenzoyl)-1-ethyl-3-methyl-5-pyrazolyl tosylate 0.37 g (1 mmol) of 4-(4-Trifluoromethyl-2-methylsulfonylbenzoyl)-5-hydroxy-1-ethyl-3-methylpyrazole and 0.20 g (1.1 mmol) of p-Tos-Cl were dissolved in 20 ml of $CH_3CN$. 0.26 g (1.8 mmol) of potassium carbonate was then added, and the mixture was stirred at room temperature for 12 h. The mixture was diluted with water and extracted with ethyl acetate. The extract was dried with $MgSO_4$ and concentrated. This gave 4-(4-Trifluoromethyl-2-methylsulfonylbenzoyl)-1-ethyl-3-methyl-5-pyrazolyl tosylate as a wax.

Yield: 0.51 g (98% of theory); $^1$H-NMR: δ [CDCl$_3$] 1.90 (t, 3H), 2.05 (s, 3H), 2.45 (s, 3H), 3.25 (s,3H), 4.05 (q, 2H), 7.35 (d, 2H), 7.45 (d, 1H), 7.75 (d, 2H), 8.05 (d,1 H), 8.40 (s, 1H).

The examples listed in the tables below were prepared analogously to the methods mentioned above or are obtainable analogously to the methods mentioned above.

The following abbreviations were used:

| Bn = benzyl | Bz = benzoyl | Et = ethyl | Me = methyl |
|---|---|---|---|
| Pr = propyl | Ph = phenyl | Tos = Tosyl | m.p. = Melting point |

TABLE A

Compound of the formula (I) according to the invention in which the substituents and symbols are as defined below:

$R^1 = Me \quad R^2 = CF_3 \quad n = 2$

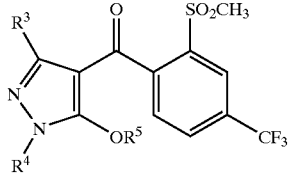

| No. | $R^3$ | $R^4$ | $R^5$ | Physical data |
|---|---|---|---|---|
| 1 | Me | E | H | $^1$H—NMR data see Preparation Example 1 |
| 2 | Me | Et | Tos | $^1$H—NMR data see Preparation Example 2 |
| 3 | Me | Et | Bz-CH$_2$ | |
| 4 | Me | Me | H | m.p. 202–204° C. |
| 5 | Me | Me | 4-F-Bz-CH$_2$ | oil |
| 6 | Me | Me | Ph-SO$_2$ | |
| 7 | Me | Me | Bz-CH$_2$ | oil |
| 8 | Me | Me | 4-NO$_2$-Bz-CH$_2$ | oil |
| 9 | Me | Me | 3-NO$_2$-Bz-CH$_2$ | oil |
| 10 | Me | Me | Tos | m.p. 130–132° C. |
| 11 | Me | Me | n-Pr-SO$_2$ | wax |
| 12 | Me | Me | Bn | m.p. 179° C. |
| 13 | Me | Me | Me-SO$_2$ | m.p. 147° C. |
| 14 | Me | Me | 2-NO$_2$-Bn | m.p. 146° C. |
| 15 | Me | Et | Me-SO$_2$ | oil |
| 16 | Me | Et | Me-SO$_2$ | oil |
| 17 | Me | Et | Bn | glasslike |
| 18 | Me | Et | 4-F-Bz-CH$_2$ | |

B. FORMULATION EXAMPLES

1. Dust

A dust is obtained by mixing 10 parts by weight of a compound of the formula (I) and 90 parts by weight of talc as inert substance and comminuting the mixture in a hammer mill.

2. Dispersible Powder

A wettable powder which is readily dispersible in water is obtained by mixing 25 parts by weight of a compound of the formula (I), 64 parts by weight of kaolin-containing quartz as inert substance, 10 parts by weight of potassium lignosulfonate and 1 part by weight of sodium oleoylmethyltaurinate as wetter and dispersant and grinding the mixture in a pinned-disk mill.

3. Dispersion Concentrate

A dispersion concentrate which is readily dispersible in water is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.) and grinding the mixture in a ball mill to a fineness of below 5 microns.

4. Emulsifiable Concentrate

An emulsifiable concentrate is obtained from 15 parts by weight of a compound of the formula (I), 75 parts by weight of cyclohexanone as the solvent and 10 parts by weight of ethoxylated nonylphenol as the emulsifier.

5. Water-dispersible Granules

Water-dispersible granules are obtained by mixing 75 parts by weight of a compound of the formula(I), 10 parts by weight of calcium lignosulfonate, 5 parts by weight of sodium lauryl sulfate, 3 parts by weight of polyvinyl alcohol and 7 parts by weight of kaolin grinding the mixture on a pinned-disk mill and granulating the powder in a fluidized bed by spraying on water as the granulation liquid.

Water-dispersible granules are also obtained by homogenizing and precomminuting, on a colloid mill, 25 parts by weight of a compound of the formula (I), 5 parts by weight of Sodium 2,2'-dinaphthylmethane-6,6'-disulfonate, 2 parts by weight of sodium oleoylmethyltaurinate, 1 part by weight of polyvinyl alcohol, 17 parts by weight of calcium carbonate and 50 parts by weight of water subsequently grinding the mixture in a bead mill and atomizing and drying the resulting suspension in a spray tower by means of a single-substance nozzle.

C. BIOLOGICAL EXAMPLES

1. Post-emergence herbicidal action on harmful plants

Seeds of monocotyledonous and dicotyledonous harmful plants are placed in sandy loam soil in cardboard pots, covered with soil and grown in a greenhouse under good growth conditions. Two to three weeks after sowing, the test plants are treated at the three-leaf stage. The compounds according to the invention which were formulated as wettable powders or emulsion concentrate are sprayed, at one of the dosages given in Tables 1 to 5, onto the surface of the green parts of the plants at an application rate of from 600 to 800 l of water/ha (converted). After the test plants had remained in the greenhouse for about 3 to 4 weeks under optimum growth conditions, the effect of the preparations is scored visually by comparison with compounds disclosed in the prior art. As shown by the results of Comparative Tables 1 to 4, the selected compounds according to the invention have better herbicidal activity against a broad spectrum of economically important monocotyledonous and dicotyledonous harmful plants than the compounds disclosed in the prior art.

2. Tolerance by Crop Plants

In further greenhouse experiments, seeds of barley and monocotyledonous and dicotyledonous harmful plants are placed in sandy loam soil, covered with soil and placed in a greenhouse until the plants had developed two to three leaves. The treatment with the compounds of the formula (I) according to the invention and, by comparison, with the compounds disclosed in the prior art is then carried out as described above under Item 1. Four to five weeks after the application and after the plants had been in the greenhouse, visual scoring reveals that the compounds according to the invention, in contrast to the compounds disclosed in the prior art, do not inflict any damage on the crop plant, even at relatively high dosages of active compound (see Table 5).

| Compounds used in the comparative experiments and disclosed in the prior art | |
|---|---|
| No. | Structure |
| S1 | (pyrazole with 4-SO2CH3 benzoyl) |
| S2 | (pyrazole with 3-CF3 benzoyl) |
| S3 | (pyrazole with 2,4-dichloro benzoyl) |

The following abbreviations were used in the comparative tables below:

| | | | |
|---|---|---|---|
| APSEV | *Apera spica venti* | CHEAL | *Chenopodium album* |
| LAMPU | *Lamium purpureum* | POLCO | *Polygonum convolvulus* |
| STEME | *Stellaria media* | VERHE | *Veronica hederifolia* |
| VERPE | *Veronica persica* | VIOTR | *Viola tricolor* |
| HORVS | *Hordeum vulgaris* | | |

Comparative Table 1

| Compound | | Damage to the harmful plants in % | | |
|---|---|---|---|---|
| No. | Dosage [g off a.i./ha] | POLCO | VERHE | VIOTR |
| 4 from Table A | 200 | 90 | 90 | 80 |
| S1 | 200 | 20 | 30 | 30 |

Comparative Table 2

| Compound | | Damage to the harmful plants in % | | |
|---|---|---|---|---|
| No. | Dosage [g off a.i./ha] | CHEAL | POLCO | STEME |
| 10 from Table A | 50 | 95 | 60 | 70 |
| S2 | 50 | 0 | 10 | 10 |

Comparative Table 3

| Compound | | Damage to the harmful plants in % | |
|---|---|---|---|
| No. | Dosage [g off a.i./ha] | CHEAL | STEME |
| 4 from Table A | 100 | 90 | 85 |
| S2 | 100 | 0 | 10 |

Comparative Table 4

| Compound | | Damage to the harmful plants in % | | |
|---|---|---|---|---|
| No. | Dosage [g off a.i./ha] | LAMPU | VERHE | VERPE |
| 8 from Table A | 50 | 70 | 60 | 100 |
| S3 | 50 | 20 | 10 | 10 |

Comparative Table 5

| Compound | | Damage to the useful plants in % |
|---|---|---|
| No. | Dosage [g off a.i./ha] | HORVS |
| 1 from Table A | 200 | 0 |
| 4 from Table A | 200 | 0 |
| S2 | 200 | 20 |
| S3 | 200 | 20 |

What is claimed is:

1. A benzoylpyrazole of the formula (I) or a salt thereof

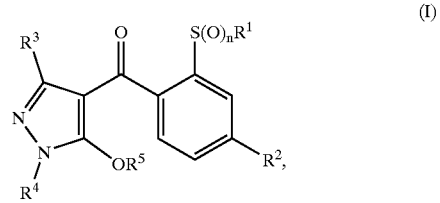

(I)

in which $R^1$ is methyl or ethyl;

$R^2$ is trifluoromethyl;

$R^3$ is hydrogen, methyl or ethyl;

$R^4$ is methyl, ethyl or n-propyl;

$R^5$ is hydrogen, $(C_1-C_6)$-alkylcarbonylmethyl, $(C_1-C_4)$-alkylsulfonyl, phenylsulfonyl, benzyl, benzoylmethyl, $(C_1-C_3)$-alkylsulfonyl which is mono- or polysubstituted by halogen, phenylsulfonyl which is monosubstituted by methyl or halogen, benzyl which is substituted by halogen, nitro, methyl or methoxy or benzoylmethyl which is mono- or polysubstituted by halogen, nitro, methyl or methoxy and n is 0, 1, or 2.

2. A benzoylpyrazole as claimed in claim 1, in which $R^1$ is methyl and $R^3$ is hydrogen or methyl.

3. A benzoylpyrazole as claimed in claim 1, in which $R^4$ is methyl or ethyl.

4. A benzoylpyrazole as claimed in claim 1, in which $R^5$ is hydrogen, methylsulfonyl, ethylsulfonyl, n-propylsulfonyl, phenylsulfonyl, 4-methylphenylsulfonyl, benzyl, benzoylmethyl, nitrobenzoylmethyl or 4-fluorobenzoylmethyl.

5. A benzoylpyrazole as claimed in claim 1, in which $R^3$ is methyl.

6. A herbicidal composition which comprises a herbicidally effective amount of at least one compound of the formula (I) as claimed in claim 1.

7. The herbicidal composition as claimed in claim 6 in a mixture with formulation auxiliaries.

8. A method for controlling undesirable plants, which comprises applying an effective amount of at least one compound of the formula (I) as claimed in claim 1 or a herbicidal composition as claimed in claim 6 or 7 on to the plants or the location of the undesirable vegetation.

9. The method as claimed in claim 8, wherein the compounds of the formula (I) are used for controlling undesirable plants in crops of useful plants.

10. The method as claimed in claim 9, wherein the useful plants are transgenic useful plants.

\* \* \* \* \*